United States Patent

Gärtner et al.

[11] Patent Number: 5,838,491
[45] Date of Patent: Nov. 17, 1998

[54] VIEWING APPARATUS HAVING OBLIQUE ILLUMINATION

[75] Inventors: Hartmut Gärtner, Oberkochen; Ulrich Lemcke, Heidenheim; Christian Lücke, Oberkochen; Joachim Steffen, Westhausen, all of Germany

[73] Assignee: Carl-Zeiss-Stiftung, Heidenheim, Germany

[21] Appl. No.: 890,931

[22] Filed: Jul. 10, 1997

[30] Foreign Application Priority Data

Jul. 15, 1996 [DE] Germany ................. 196 28 417.1

[51] Int. Cl.⁶ .................. G02B 21/06; G02B 21/00
[52] U.S. Cl. ............. 359/385; 359/368; 359/383
[58] Field of Search ........................ 359/368–373, 359/375–381, 383–390; 351/240, 243

[56] References Cited

U.S. PATENT DOCUMENTS 5,253,106 10/1993 Hazard ........................ 359/368
5,748,367 5/1998 Lucke et al. ................ 359/385

FOREIGN PATENT DOCUMENTS

| 4016166 | 2/1991 | Germany | 359/385 |
| 4214445 | 11/1993 | Germany | 359/385 |
| 595788 | 5/1994 | Germany | 359/385 |
| 4243488 | 6/1994 | Germany | 359/385 |
| 6-138392 | 5/1994 | Japan | 359/385 |

*Primary Examiner*—Thong Nguyen
*Attorney, Agent, or Firm*—Walter Ottesen

[57] ABSTRACT

A viewing arrangement includes an objective (5) having a variable intersection distance and an intersection-distance dependent oblique illumination (7) which is separate from the objective (5). The oblique illumination (7) includes two illuminating beam paths (9, 11) for completely illuminating contoured objects without shadows. The illuminating beam paths (9, 11) are inclined toward each other ahead of the object (13, 16) to be viewed. The mutual inclination of the two illuminating beam paths (9, 11) is dependent upon the particular intersection distance of the objective (5).

11 Claims, 4 Drawing Sheets

VIEWING APPARATUS HAVING OBLIQUE ILLUMINATION

FIELD OF THE INVENTION

The invention relates to a viewing apparatus having a viewing optic which includes an objective of variable intersection distance and an oblique illumination which is separate from the objective and is dependent upon the intersection distance.

BACKGROUND OF THE INVENTION

For an illumination separate from the objective, the illuminating light reaches the viewing field without passing through the objective or a portion thereof. An illumination of this kind separate from the objective is preferred, for example, when any of the following are unacceptable: a reduction of the illumination because of optical dividers in the viewing beam path, an increased tendency to incident light reflections in a multi-lens objective and a relatively large structural height caused by optical dividers or deflecting elements in the viewing beam path.

A viewing device of the above kind is disclosed in U.S. patent application Ser. No. 08/544,794, filed Oct. 18, 1995, now U.S. Pat. No. 5,748,367. This application describes a stereomicroscope which is preferably used as a surgical microscope. The objective of this microscope has a variable intersection distance which permits focussing of objects or object regions which are at different distances away. In this multi-lens objective, an illumination coaxial to the optical axis of the viewing optic would have incident light reflections associated therewith. Further, the smallest possible structural elevation is wanted in a surgical microscope. For these reasons, the object to be viewed is illuminated by the incident light at an angle (via a deflecting mirror) by an illuminating optic mounted transverse to the viewing optic. The deflecting mirror is mounted laterally next to the objective and can be pivoted with respect to the illuminating light beam in order to illuminate the object to be viewed, even at changed intersection distance of the objective, with the illuminating light being centered to the optical axis of the illuminating optic. The intersection-distance dependency of this oblique illumination is caused by the coupling of the inclination change of the deflecting mirror to the intersection distance change of the objective.

However, problems occur with this known viewing arrangement when the object to be viewed has recesses and/or depressions. It is then possible that the illuminating radiation, which incidents inclined on the object to be viewed, is shaded by the edge of the depression and can only illuminate a portion of the base of the depression. Recesses are, however, frequent, for example, in neurosurgery, a preferred area of application of surgical microscopes. These depressions can be in the form of relatively narrow channels through which the surgeon must penetrate to the actual surgical target. In surgical microscopes, a large structural height of the microscope can lead to an unacceptable large distance between the head of the surgeon and the region to be operated on. For this reason, a coaxial illumination, which incidents perpendicularly on the base of the depression, cannot be used because a coaxial illumination would require additional optical elements in the viewing beam path.

SUMMARY OF THE INVENTION

It is an object of the invention to provide a viewing apparatus having an inclined illumination which is separate from the objective and is dependent upon the intersection distance. It is a further object of the invention to provide such a viewing apparatus with which it is possible to also illuminate objects having regions of different depth with the illumination being substantially free of shadows.

In the viewing apparatus, an objective has a variable intersection distance and an intersection-distance dependent oblique illumination which is separate from the objective. The oblique illumination includes two illuminating beam paths for completely illuminating contoured objects without shadows. The mutual inclination of the two illuminating beam paths is dependent upon the particular intersection distance of the objective.

In this way, the object region, which is not illuminated by the one viewing beam path because of its inclined incidence on the object, can be illuminated by the illuminating beam of the other illuminating beam path. According to the invention, the other illuminating beam path is inclined with respect to the first illuminating beam path and can therefore back illuminate shadow regions of the first illuminating beam path. With a variable objective intersection distance, a trouble-free illumination of the object to be viewed can be guaranteed only by the intersection-distance dependency of the mutual inclination of the two viewing beam paths. The illumination of the object to be viewed is, for example, centered with respect to the optical axis of the viewing optic.

From the foregoing, it can be seen that the advantages of the viewing apparatus of the invention can be achieved also with more than two intersection-distance dependent illuminating beam paths inclined with respect to each other.

In one embodiment, the two illuminating beam paths are at respective sides of the optical axis of the viewing optic and lie essentially in one plane with the latter. In this embodiment, the illuminating light components advantageously operate conjointly to provide complete illumination of the object. The illuminating light components are allocated to respective ones of the illuminating beam paths.

The two illuminating beam paths can be a main illuminating beam path and an ancillary illuminating beam path, respectively, and can originate from one light source and pass through an illuminating optic arranged transversely to the viewing optic. In this embodiment, the viewing apparatus can be operated with only one light source and a common illuminating optic can be used for both viewing beam paths. This viewing optic essentially determines the brightness and the size of the object region to be illuminated.

In this embodiment of the invention, a first deflecting element can be mounted forward of the viewing optic as seen from the light source and a second deflecting element can be mounted rearward of the viewing optic. In this embodiment, the first deflecting element can direct the main illuminating beam path onto the object to be viewed and the second deflecting element can deflect the ancillary viewing beam path onto this object. Additional deflecting elements can direct the ancillary illuminating beam path around the viewing optic onto the second deflecting element. In this way, it is ensured in a simple manner that the two illuminating beam paths are separate from the objective, that is, incident light reflections can be avoided and the structural height is low.

In another embodiment of the invention, at least one lens element is provided in the ancillary illuminating beam path in order to sharply image an illuminating field diaphragm on the object to be viewed via the ancillary viewing beam path. On the one hand, a lens of negative refractive power can compensate the longer light path in the ancillary illuminating beam path and, on the other hand, an additional lens of positive refractive power can control the size of the illuminating field.

In a realization of the invention which is constructively advantageous and is of especially light weight, the first deflecting element can be a first deflecting mirror having an intersection-distance dependent inclination and be rotatable about a first rotational axis and the second deflecting element can be a second deflecting mirror having an intersection-distance dependent inclination and be rotatable about a second rotational axis. That is, the position and orientation with respect to the optical axis of the viewing optic and with respect to the optical axis of the illuminating beam path assigned thereto are determined by the instantaneous intersection distance of the objective.

The ancillary illuminating beam path can run coaxially to the second rotational axis forward of the deflection at the second deflecting mirror. In this case, the additional illuminating beam path can be arranged in a hollow rotational shaft embodying the rotational axis. In this way, space is saved and the relationship between the change of intersection distance of the objective and the change of inclination of the second deflecting mirror is relatively simple.

A device separate for each deflecting mirror and which adjusts the inclination of the particular mirror to the instantaneous intersection distance of the objective can be omitted if a coupling device couples the change of inclination (which takes place for a change of intersection distance of the objective) of the first deflecting mirror with a corresponding deflection of the second deflecting mirror.

An especially space-saving and play-free coupling device includes a coupling rod pivotally connected eccentrically to the first rotatable shaft and pivotally connected to the second rotatable shaft. In this way, and by a suitable selection of the particular spacings of the pivot points from the rotational axis and the spacing of the two pivot points on the connecting rod, a rotation of the first and of the second deflecting mirror by respective desired angular amounts can be achieved in a simple manner. Here, it is noted that the first deflecting mirror must be rotated by an angular amount different than the second deflecting mirror for an intersection-distance change in the normal case.

A first rotatable shaft rotates the first deflecting mirror and a second rotatable shaft rotates the second deflecting mirror and the coupling rod is pivotally connected to a first lever arm (which is connected fixedly to the first rotatable shaft) and, with its other end, to a second pivot arm (which is connected fixedly to the second rotatable shaft). In this situation, a spring can render the coupling device free of play by pretensioning the second lever arm in the direction toward the first lever arm.

In accordance with another embodiment of the invention, an especially simple, precise and reliable mechanism is provided for controlling the inclination of an oblique-illuminating deflecting mirror connected to a rotatable shaft in a viewing apparatus of the invention equipped with intersection-distance dependent oblique illumination. A control lever connected to the first rotatable shaft is supported on a control cam which moves for an intersection-distance change of the objective.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
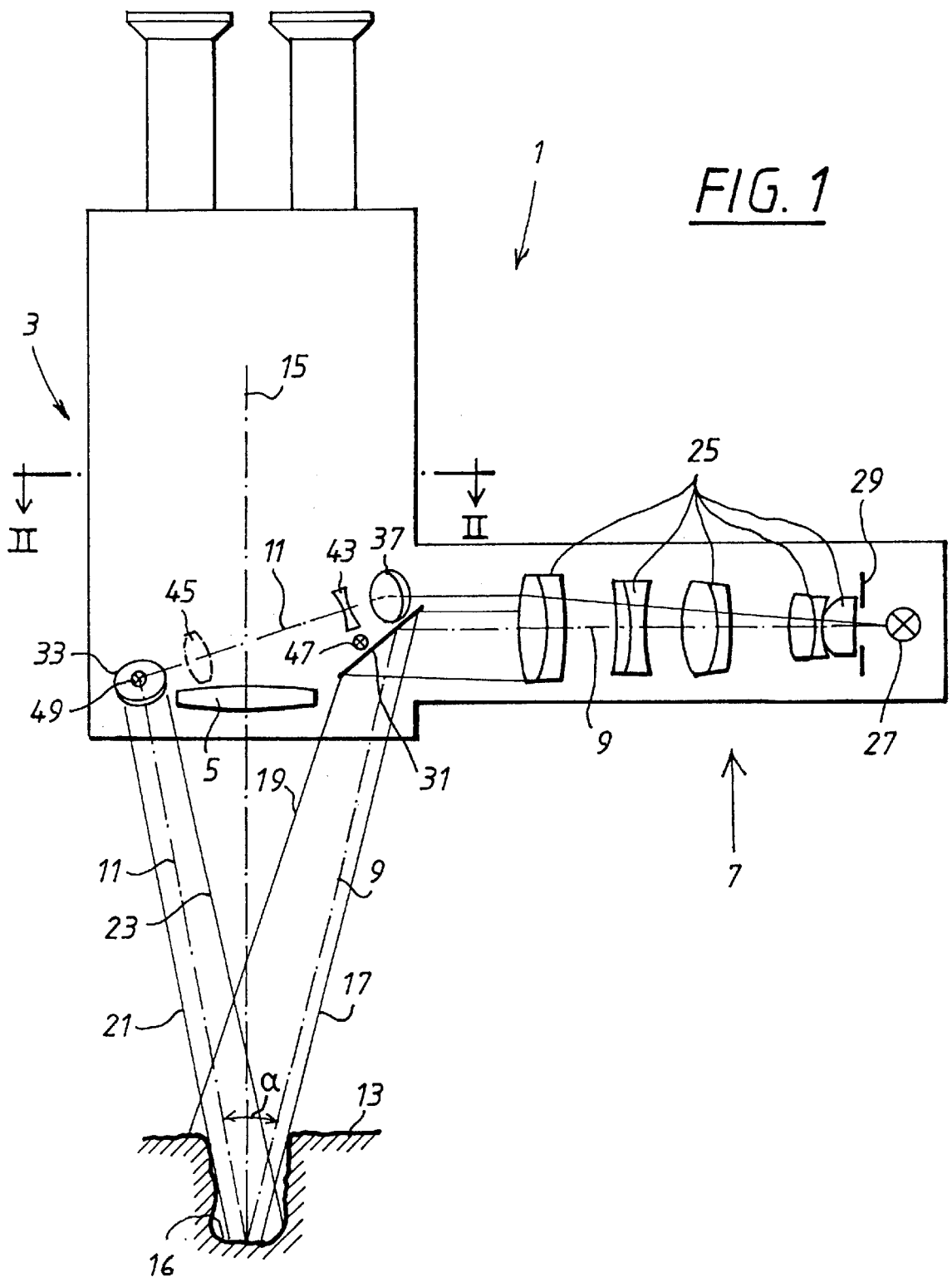
FIG. 1 is a schematic side elevation view of a viewing apparatus according to the invention.

FIG. 1 is a schematic side elevation view of an embodiment of the viewing arrangement of the invention in the form of a stereomicroscope 1. The stereomicroscope 1 includes a viewing optic 3 which includes an objective 5. The objective 5 includes several lens groups and makes varying the intersection distance possible by mutual displacement of these lens groups. The stereomicroscope 1 further includes an illuminating arrangement 7 having a main illuminating beam path 9 and an ancillary illuminating beam path 11. These beam paths 9 and 11 run inclined to the optical axis 15 of the viewing optic 3 forward of the object 13 to be viewed. The illuminating arrangement 7 therefore effects an oblique illumination in the incident light.

The two illuminating beam paths 9 and 11 are intersection-distance dependently inclined, that is, they conjointly define an angle α which is dependent upon the particular intersection distance of the objective 5. The intersection distance is determined by the distance of the object Haarea 16, which is to be viewed, from the objective 5. The illuminating beam paths 9 and 11 and the optical axis 15 intersect at the particular intersection distance for centrally illuminating the viewing field.

The illuminating beam path 9 is shown in FIG. 1 as are the outer rays 17 and 19 of the main illumination and, in addition, the ancillary illuminating beam path 11 and the outer rays 21 and 23. In FIG. 1, the object area 16 to be viewed is defined by the base of a depression of the object 13. For this reason, a complete illumination of the object area 16 to be viewed is obtained only with the two illuminating beam paths 9 and 11 together.

The illuminating arrangement 7 includes an illuminating optic 25 arranged transversely to the viewing optic 3. The illuminating optic 25 images an illuminating field diaphragm 29 in the main illuminating beam path 9 via a deflecting mirror 31 onto the object area 16 to be viewed. The field diaphragm 29 is illuminated by a light source 27. A detailed description of an illuminating optic 25 as described above is disclosed in U.S. patent application Ser. No. 08/544,794, filed Oct. 18, 1995, which is incorporated herein by reference.

The ancillary illuminating beam path 11 is deflected via a deflecting mirror 33 in the direction toward the object 13. The ancillary illuminating beam path 11 also passes through the illuminating optic 25 and detours around the deflecting mirror 31 or reaches a mirror 37 through a cutout in the deflecting mirror 31 and is reflected by mirror 37 onto a further mirror 39 shown in FIG. 2. From the mirror 39, the ancillary illuminating beam path 11 is reflected onto a mirror 41 (shown in FIG. 2) and by the mirror 41 to the deflecting mirror 33. The light path in the ancillary illuminating beam path 11 is longer compared to the main illuminating beam path 9. A lens 43 having negative refractive power is mounted in the ancillary illuminating beam path 11 between the mirrors 39 and 41 in order to sharply image the illuminating field diaphragm 29 on the object area 16 to be viewed via the ancillary illuminating beam path 11 notwithstanding the longer light path in the ancillary illuminating beam path 11. In addition, the size of the viewing field of the ancillary illuminating beam path 11 can be influenced by a lens 45 in the ancillary illuminating beam path 11. The lens 45 is shown in phantom outline in FIG. 1 and has a positive refractive index.

The deflecting mirror 31 is pivotable about an axis 47 in order to achieve the intersection-distance dependent inclination of the illuminating beam paths 9 and 11 to each other. The axis 47 is orthogonal to the plane of the drawing as well as to the component area of the illuminating beam path 9 which passes through the illuminating optic 25 and is parallel to the mirror surface of the deflecting mirror 31. The deflecting mirror 33 of the ancillary illuminating beam path 11 is rotatable about a rotational axis 49 parallel to the rotational axis 47. The rotational axis 49 passes through the deflecting mirror 33 at an angle. The rotation of the mirrors 31 and 33 is controlled by the intersection distance change of the objective 5 and will be explained with respect to FIGS. 3 to 5.

Figure 2:
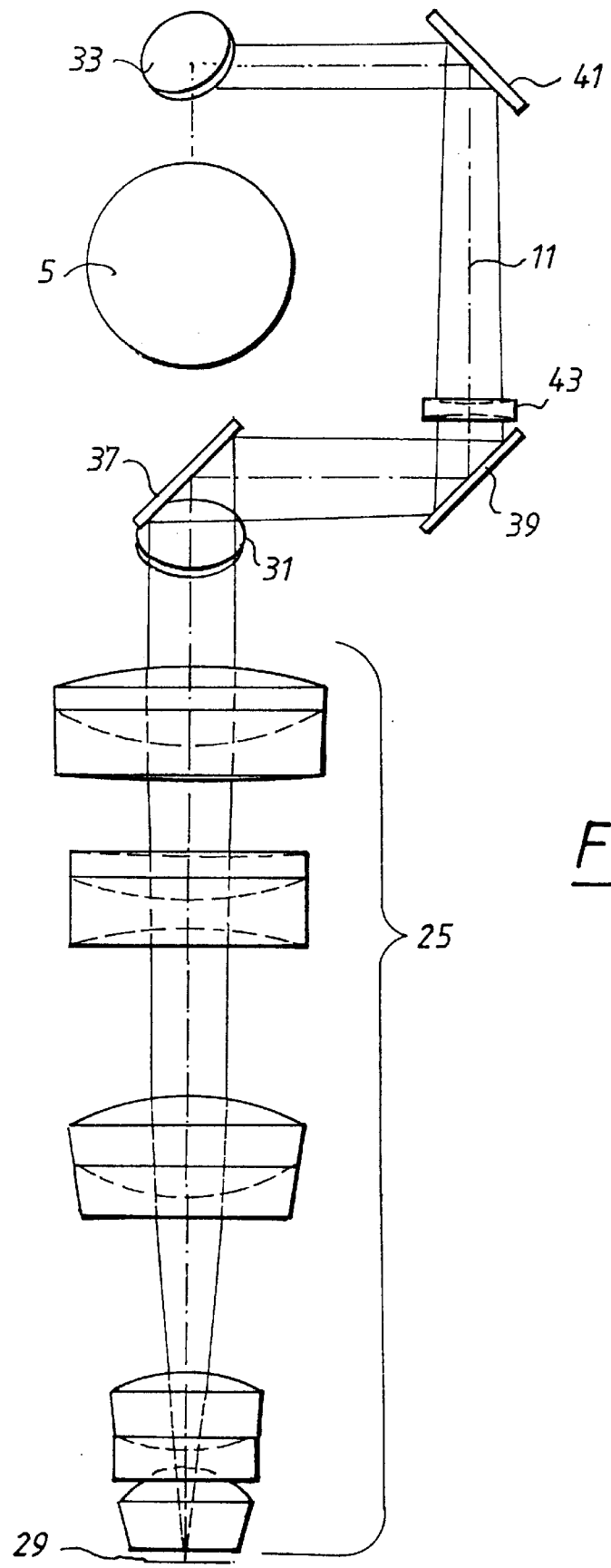
FIG. 2 is a schematic section view of FIG. 1 taken in the direction of arrows II—II of FIG. 1.

In FIG. 2, the ancillary illuminating beam path 11 is shown from the plane of the field diaphragm 29 to the intersection-distance dependent rotatable deflecting mirror 33 with the outer light rays of a beam emanating from a point of the plane of the field diaphragm 29. The elements of FIG. 1 are shown in FIG. 2 with the same reference numerals as in FIG. 1.

FIG. 2 shows that the ancillary illuminating beam path 11 is separate from the objective 5; that is, the objective 5 is neither penetrated nor even touched in passing. The invention, however, includes not only this embodiment of FIG. 2 but also embodiments wherein the ancillary illuminating beam path crosses the optical axis of the viewing optic and therefore is guided above or below the objective or even between individual objective lens groups to the deflecting mirror 33 without touching the objective lenses.

The ancillary illuminating beam path 11 impinges on the mirror 37 inclined and decentered with respect thereto. The mirror 37 is tilted by 45√ sagittally and by 2° tangentially with reference to the optical axis of the illuminating optic 25 in order to guide the ancillary illuminating beam path 11 centered to the mirrors (39, 41 and 33) and centered to the diverging lens 43. The ancillary illuminating beam path 11 runs between the mirrors 37 and 39 and between the mirror 41 and the deflecting mirror 33 in a plane which is orthogonal to the optical axis 15 of the viewing optic. In contrast, the illuminating beam path 11 runs inclined between the mirrors 39 and 41 because the deflecting mirror 33 is mounted closer to the object 13 than the mirror 31. With this arrangement of the deflecting mirror 33, the light path in the ancillary illuminating beam path 11 is shorter than in a beam path running in a plane up to the deflecting mirror 33. Furthermore, and in this way, the opening, which is assigned to the ancillary illuminating beam path 11, in the housing of the stereomicroscope 1 can be smaller for the same deflecting mirror pivot range as for a deflecting mirror further remote from the object 13 and therefore further from the stereomicroscope housing.

Figure 3:
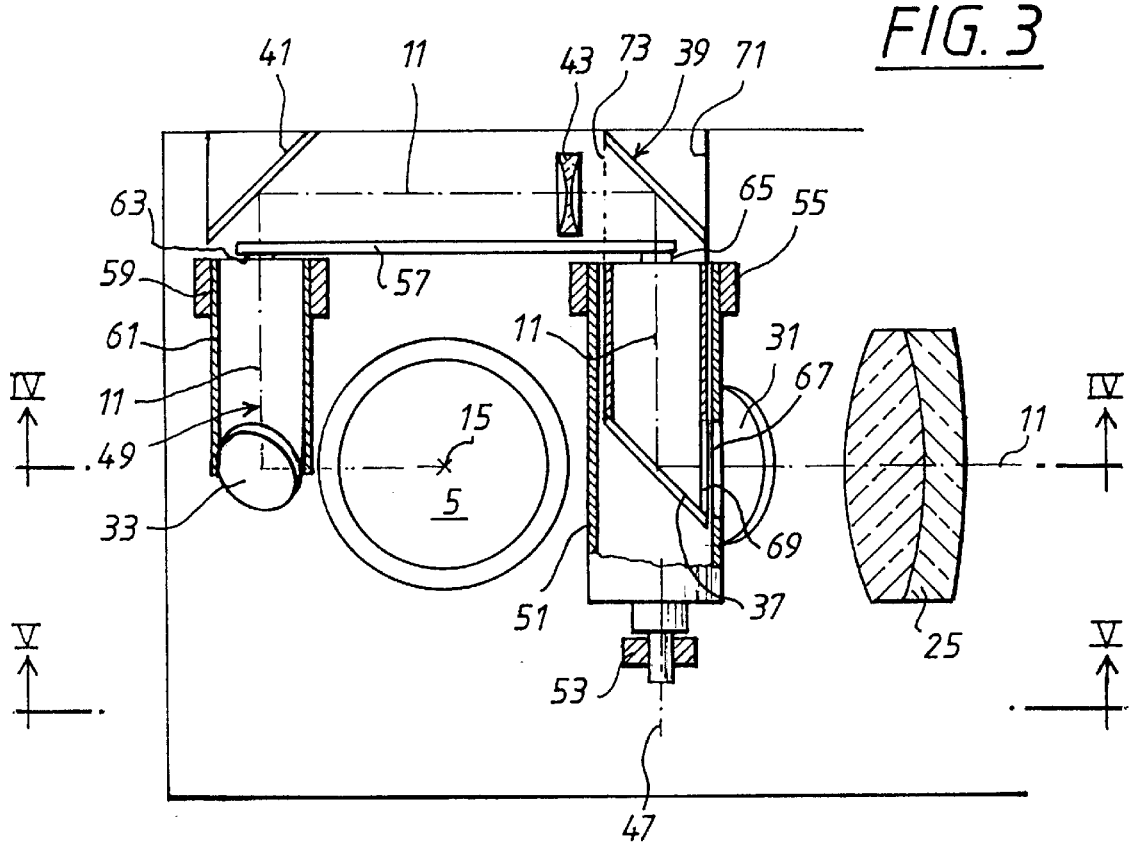
FIG. 3 is a detailed view, partially in section, likewise seen in the direction of arrows III—III of FIG. 5.

FIG. 3 is a detailed section view corresponding to FIG. 2. The elements in FIG. 3 have the same reference numerals as in FIGS. 1 and 2.

In FIG. 3, a control lever 53 is mounted on a hollow shaft 51 so as to rotate therewith. The hollow shaft 51 is rotatable about the rotational axis 47 of the deflecting mirror 31 and the control lever 53 is pivoted for an intersection distance change of the objective 5 and pivots the hollow shaft 51. This control lever 53 pivots the deflecting mirror 31 via the hollow shaft 51 in such a manner that the illuminating field of the main illumination remains centered in the object plane about the optical axis 15 of the viewing optic 3. In addition, a lever 55 is mounted on the hollow shaft 51 so as to rotate therewith. A coupling rod 57 is hinge connected at its one end 65 to the lever 55 at a spacing from the rotational axis 47. With its other end, the coupling rod 57 is connected at 63 to a further lever 59 at a spacing to the second rotational axis 49. The lever 59 is connected to a hollow shaft 61 so as to rotate therewith. The hollow shaft 61 holds the second deflecting mirror 33 and can be rotated about the second rotational axis 49.

Figure 4:
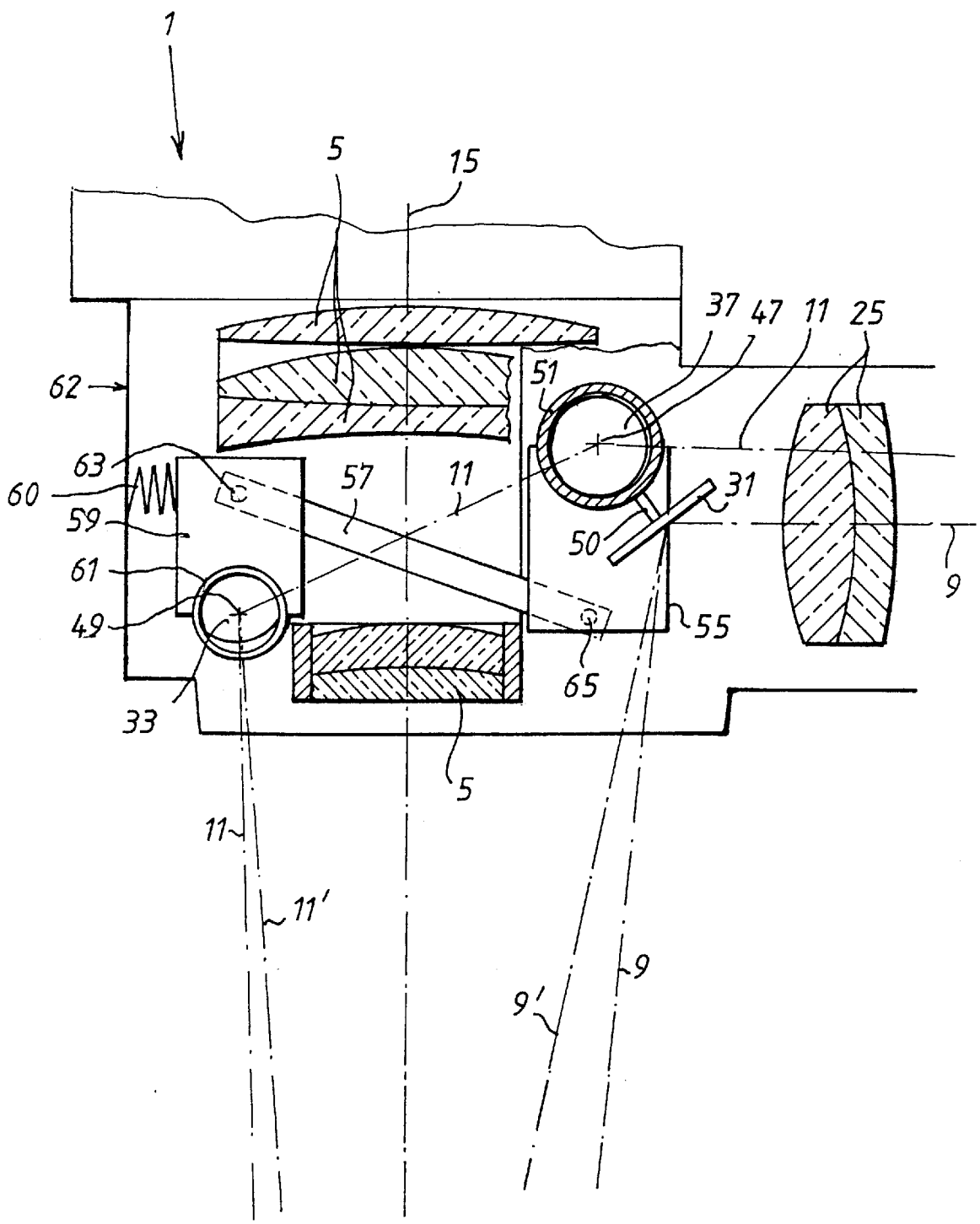
FIG. 4 is a detail view corresponding to FIG. 3 and taken in axial longitudinal section with respect to the optical axis of the viewing optic seen in the direction of arrows IV—IV of FIG. 3; and, FIG. 5 is a side elevation view, partially in section, as viewed in the direction of arrows V—V of FIG. 3.

The coupling device shown in FIG. 4 couples the inclination change of the first deflecting mirror 31 and the inclination change of the second deflecting mirror 33 to each other. The coupling device is shown in FIG. 4 in a section view in the direction of arrows IV—IV of FIG. 3. The region of the coupling rod 57 covered by the levers 55 and 59 is shown in phantom be outline in FIG. 4.

The pivot-connection point of the end of the coupling rod 57 with the lever 59 and the pivot-connection point of the other end of coupling rod 57 to the lever 55 are identified by reference numerals 63 and 65, respectively. FIG. 4 shows how a transfer of the rotational movement of the first deflecting mirror 31 to a corresponding rotational movement of the second deflecting mirror 33 is realized by the eccentric pivot connection of the coupling rod 57 with respect to the rotational axes 47 and 49. By a suitable selection of the spacing of the pivot-connection point 63 from the second rotational axis 49 and by a suitably selected spacing of the pivot-connection point 65 from the first rotational axis 47 and by a suitably selected spacing between the pivot-connection points 63 and 65, a step-up or step-down ratio is provided in correspondence to the position and orientation of the respective deflecting mirrors 33 and 31.

A pressure spring 60 is provided between the microscope housing wall 62 and the lever 59 and resiliently biases the lever 59 in the direction toward the lever 55. In this way, the coupling device is free of play at its pivot-connection points 63 and 65.

In FIG. 4, it can also be seen that the first deflecting mirror 31 is fixedly connected to the rotational shaft 51 via an intermediate piece 50. The first deflecting mirror 31 can, however, also be directly cemented to the rotational shaft 51.

The illuminating beam paths identified in FIG. 4 by reference numerals 9' and 11' correspond to an intersection distance of the objective 5 which is approximately half compared to the intersection distance corresponding to the illuminating beam paths 11 and 9. It can be seen that the deflecting mirrors 31 or 33 must be rotated by different angular amounts when there is a change of the intersection distance.

In FIG. 3, the deflection of the ancillary illuminating beam path 11 around the objective 5 will now be explained.

The illuminating beam path 11 runs through an opening 67 in the hollow shaft 51 and through an opening 69 in a hollow cylinder 71 and impinges on the spatially fixed mirror 37. The hollow cylinder 71 is mounted within the hollow shaft 51 so that it is nonrotatable and the mirror 37 is held by the hollow cylinder 71 which extends into the hollow shaft 51 coaxially to the rotational axis 47. The illuminating beam path 11 is directed by the mirror 37 to the mirror 39 and thereafter through an opening 73 in the hollow cylinder 71 and through the diverging lens 43 onto the mirror 41. The mirror 41 is fixedly connected to the housing of the microscope 1 and the mirror 39 is held fixedly in place in the hollow cylinder 71. The mirror 41 directs the illuminating beam path 11 coaxially to the rotational axis 49 to the second deflecting mirror 33 which is held at one end by the hollow shaft 61. This second deflecting mirror 33 deflects the ancillary illuminating beam path 11 through an opening of the hollow shaft 61 onto the object 13 to be viewed. The opening is obscured by the deflecting mirror 33 and can therefore not be seen.

Figure 5:
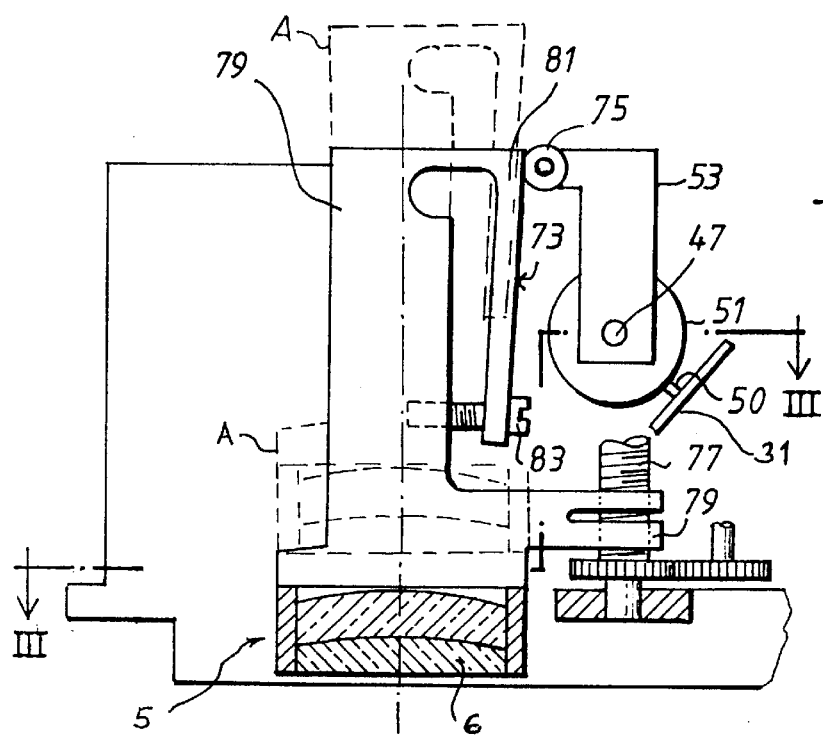

In FIG. 5, the mechanism which effects the focal-intercept dependent inclination of the first deflecting mirror 31 is shown while omitting the second deflecting mirror 33. Here, the same reference numerals are used for the same elements as in the previous FIGS.

The control lever 53 of FIG. 3 is shown in FIG. 5 in side elevation. Likewise, the rotatable hollow shaft 51 can also be seen although partially obscured by the control lever 53. The control lever 53 is fixedly clamped to hollow shaft 51 so that it cannot rotate relative thereto. In this way, the control lever 53 is fixedly connected to the lever 55 shown in FIG. 4 and therefore resiliently biased in the direction toward an intersection-distance changing element 79 by the spring 60 also shown in FIG. 4. The intersection-distance changing element 79 is displaceable by a spindle 77 (partially shown) along the optical axis 15 of the viewing optic.

This intersection-distance changing element 79 is displaceable by the spindle 77 along the optical axis 15 of the viewing optic. The control lever 53 is supported via a roller bearing 75 on a surface 73 which defines a control cam and is arranged on the intersection-distance changing element 79. The intersection-distance changing element 79 and therefore the control cam 73 is connected to the lens group(s) 6 of the objective 5 which is displaced to change the intersection distance of the objective 5. A position of this lens group 6 (after being displaced) is shown in phantom outline at A together with the position of the control cam 73.

The control cam 73 is configured on a tongue 81 of the intersection-distance changing element 79 which is resiliently biased by an adjusting screw 83 in the direction toward the optical axis 15 and is curved. The adjusting screw 83 passes through the tongue 81 and engages in the intersection-distance changing element 79. With a displacement of the intersection-distance changing element 79, a pivoting of the control lever 53 is effected under the action of the spring 60 of FIG. 4. The displacement of the intersection-distance changing element 79 takes place with a roll off of the roller bearing 75 on the control cam 73. This action takes place because the control cam 73 is curved inwardly toward the optical axis 15. This leads directly to the intersection-distance dependent pivoting of deflecting mirror 31 because of the connection of the control lever 53 to the hollow shaft 51 so that the control lever 53 cannot rotate relative to the latter.

This mechanism requires only few components to couple the inclination of the deflecting mirror 31 and the particular intersection distance of the objective 5 and is extremely compact, precise and reliable. Furthermore, an adjustment can be carried out in a simple manner by a corresponding selection of the depth of penetration of the screw 83 in the main body of the intersection-distance changing element 79.

It is understood that the foregoing description is that of the preferred embodiments of the invention and that various changes and modifications may be made thereto without departing from the spirit and scope of the invention as defined in the appended claims.

What is claimed is:

1. A viewing apparatus for viewing an object comprising:
    viewing optics defining an optical axis and including an objective defining an intersection distance;
    a device for adjusting said intersection distance of said objective;
    an illuminating assembly including a first set of optics for guiding a first illuminating beam to said object along a first illuminating beam path; and, a second set of optics for guiding a second illuminating beam to said object along a second illuminating beam path;
    said first and second illuminating beam paths being inclined to each other at an angle at a location forward of said object; and,
    a device for interconnecting said sets of optics and said adjusting device so as to cause said angle to be dependent upon said intersection distance.

2. The viewing apparatus of claim 1, said first and second illuminating beam paths being on respective sides of said optical axis; and, said optical axis and said first and second illuminating beam paths all lying essentially in a single plane.

3. The viewing apparatus of claim 1, said illuminating assembly including a light source and illuminating optics mounted transversely to said viewing optics; said first illuminating beam being a main illuminating beam and said second illuminating beam being an ancillary illuminating beam; said first set of optics having a first part and a second part; said second set of optics likewise having a first part and a second part; said first part of said first set of optics and said first part of said second set of optics being conjointly defined by said illuminating optics so that both said main illuminating beam and said ancillary illuminating beam pass through said illuminating optics.

4. The viewing apparatus of claim 3, said second part of said first set of optics including a first deflecting element mounted on a first side of said optical axis for directing said main illuminating beam onto said object; and, said second part of said second set of optics including a second deflecting element mounted on a second side of said optical axis for deflecting said ancillary illuminating beam onto said object.

5. The viewing apparatus of claim 4, said second part of said second set of optics including a plurality of additional deflecting elements for deflecting said ancillary illuminating beam around said viewing optics to said second deflecting element.

6. The viewing apparatus of claim 5, said illuminating optics including an illuminating field diaphragm; and, said second part of said second set of optics including at least one lens element for imaging said illuminating field diaphragm on said object.

7. The viewing apparatus of claim 6, said interconnecting device including a first rotatable shaft and said first deflecting element being mounted on said first rotatable shaft so as to be rotatable therewith; a second rotatable shaft and said second deflecting element being mounted on said second rotatable shaft so as to be rotatable therewith; and, a connecting mechanism connecting said first and second rotatable shafts to each other and to said adjusting device whereby said first and second deflecting elements assume respective inclinations dependent upon the intersection distance to which said adjusting device has set said objective.

8. The viewing apparatus of claim 7, wherein at least one of said additional deflecting elements is so positioned that said ancillary illuminating beam is coaxial to said second rotatable shaft before being deflected at said second deflecting element.

9. The viewing apparatus of claim 7, said connecting mechanism including a connecting rod assembly eccentrically interconnecting said first and second rotatable shafts to each other.

10. The viewing apparatus of claim 9, said connecting rod assembly further including a first lever fixedly connected to said first rotatable shaft and a second lever fixedly connected to said second rotatable shaft; a connecting rod having a first end pivotally connected to said first lever and a second end pivotally connected to said second lever; and, a spring resiliently biasing said second lever toward said first lever whereby said connecting rod assembly is free of play.

11. A viewing apparatus for viewing an object comprising:

viewing optics defining an optical axis and including an objective defining an intersection distance;

a device for adjusting said intersection distance of said objective; said adjusting device including a control cam mounted on said objective for movement therewith as said intersection distance of said objective is adjusted;

an illuminating assembly for guiding an illuminating beam to said object along an illuminating path;

said illuminating assembly including a deflecting mirror for deflecting said illuminating beam onto said object; said deflecting mirror being mounted on a rotatable shaft defining a rotational axis; a lever fixedly mounted to said rotatable shaft so as to rotate therewith; and, a contact interface between said lever and said control cam whereby a rotational movement is imparted to said rotatable shaft via said lever to, in turn, tilt said deflecting mirror so as to change said illuminating beam path in dependence upon said intersection distance.

* * * * *

UNITED STATES PATENT AND TRADEMARK OFFICE
CERTIFICATE OF CORRECTION

PATENT NO. : 5,838,491
DATED : November 17, 1998
INVENTOR(S) : Hartmut Gaertner, Ulrich Lemcke, Christian Luecke and Joachim Steffen It is certified that error appears in the above-identified patent and that said Letters Patent is hereby corrected as shown below:

In column 4, line 33: delete "Haarea" and substitute -- area -- therefor.

In column 5, line 43: delete "45√" and substitute -- 45° -- therefor.

In column 6, line 23: delete "be".

Signed and Sealed this

Tenth Day of August, 1999

Attest:

Attesting Officer

Q. TODD DICKINSON

Acting Commissioner of Patents and Trademarks